United States Patent [19]

Aharon

[11] Patent Number: 5,629,746

[45] Date of Patent: May 13, 1997

[54] REMOTE IMAGE MAGNIFYING DEVICE

[76] Inventor: Oren Aharon, 23 Shikma St., Haifa 34739, Israel

[21] Appl. No.: 494,877

[22] Filed: Jun. 26, 1995

[30] Foreign Application Priority Data

Jun. 28, 1994 [IL] Israel ......... 110143

[51] Int. Cl.$^6$ .......... G02C 7/08; G02C 1/00; H04N 13/00
[52] U.S. Cl. .......... 351/57; 351/41; 351/158; 348/53
[58] Field of Search .......... 351/158, 41, 47, 351/57; 359/802, 804, 809, 810; 606/4; 348/53, 54

[56] References Cited

U.S. PATENT DOCUMENTS

| | | |
|---|---|---|
| 4,613,219 | 9/1986 | Vogel .......... 351/209 |
| 4,907,860 | 3/1990 | Noble .......... 351/158 |
| 5,414,459 | 5/1995 | Bullwinkel .......... 348/53 |

*Primary Examiner*—Hung Dang
*Attorney, Agent, or Firm*—Browdy and Neimark

[57] ABSTRACT

Fiber-optic imaging bundles are used to transfer images of an object from an objective lens to a eyepiece mounted on a portion of the front surface of a spectacle lens. In one embodiment, the image from a single objective lens is split at the eyepiece end of the fiber bundle in order to present the image to both eyes; in another, each eye has its own objective lens, fiber bundle, and eyepiece for true stereo vision; in another, right and left images from two offset objective lens are selectively colored, as by a dichroic filter, and the two colored images are transferred through a single fiber bundle to a color separator.

4 Claims, 6 Drawing Sheets

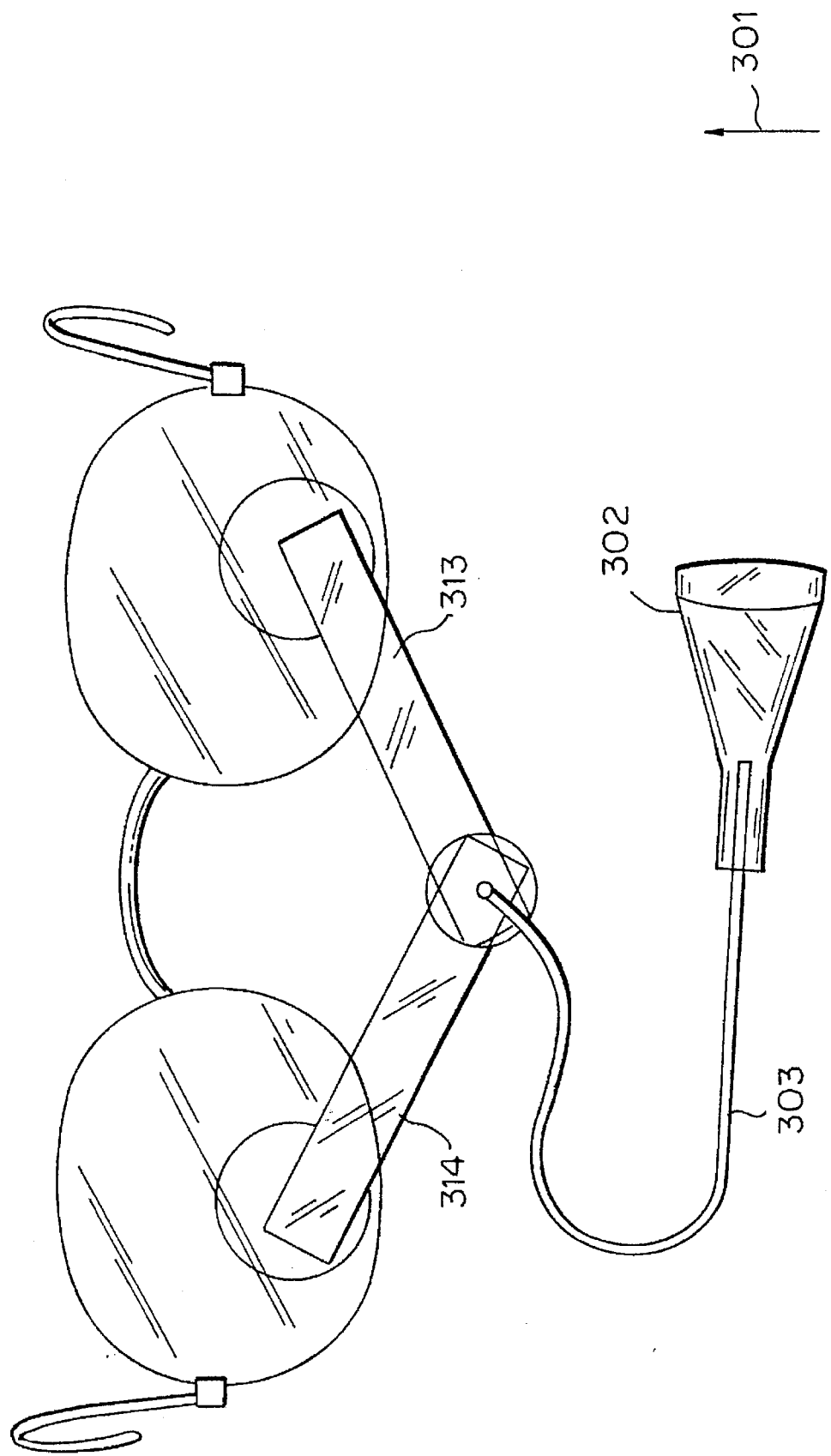

REMOTE IMAGE MAGNIFYING DEVICE

FIELD OF THE INVENTION

The present invention is in the field of image magnifying devices, specifically magnifying devices in which the observation point of the magnified image is located at a remote position with respect to the observed object. Optical magnifying devices of the kind with which the invention is concerned are applicable to the medical field or to the general inspection field.

BACKGROUND OF THE INVENTION

In the following descriptions and claims, the term "coherent fiber-optic bundle" is used to denote a fiber-optic bundle where each fiber at one end has the exact same location at the other end. The term "objective lens" is used for the lens closest to the object, and the term "eyepiece lens" for the lens closest to the eye.

Known spectacle-based magnifying systems are comprised of a combination of regular spectacles with magnifying lenses attached to the front surface of the spectacles.

The user, while observing the scene through the regular spectacles, can also observe the same magnified scene by directing his line of sight through the magnifying lens. By doing so, the user can perform delicate operations such as jewelry repair or surgery. However, for better performance, the system must have a high magnification, stereo-view, and enable observation beneath obstructed or hard-to-get-to areas. Such devices are very expensive and sometimes impossible to obtain with current technology.

While today's fiber-optic based magnification systems allow observation of obstructed areas, it does not offer the three-dimensional stereo-view needed in these dedicate operations. They are also cumbersome to use because they do not give a view of the overall scenery. The user must remove the instrument from the work area in order to gain this view. This limits the use of a fiber-scope system for monitoring remote events through the fiber system or inspecting otherwise inaccessible or hazardous area.

SUMMARY OF THE INVENTION

Accordingly, the present invention has an object, among others, to overcome deficiencies in the prior art such as noted above.

It is thus the object of the present invention to provide an improved fiber-optic based image magnification system.

In accordance with the object, the present invention provides a fiber-scope system in which the eyepiece side of the fiber-scope is attached to a user's spectacles in such a way as to allow simultaneous view of the overall scene through both the spectacles and through the fiber-scope system.

The system has several possible embodiments. The objective side of the system is usually equipped with the mechanical means for attachment to either a working tool, such as a surgeon's scalpel, or to an observation point. All of the embodiments can be equipped with a light source for improved observation.

The first and most basic embodiment, upon which all others are based, consists of a pair of spectacles equipped with mechanical means for mounting an eyepiece and a flexible fiber-optic coherent bundle attached to the eyepiece at one end and to an objective at the other end. The objective side delivers the image into the fiber bundle and the eyepiece presents the image emerging from the bundle to the user's eye.

According to a second embodiment, the image from the fiber at the eyepiece location is split into two parts by an optical beam splitter and is presented to both eyes simultaneously for improved observation and three dimensional stereo presentation.

In a third embodiment, a stereo image of a remote object is created by observing the object through two laterally offset apertures, the images from which are combined by means of dichroic filters or other optical means. The combined images are observed by the fiber-scope objective and delivered by a coherent fiber-optic bundle to be optically split into the two original images and presented to both eyes by means of a pair of eyepieces. The system has two laterally offset apertures equipped with image combining means, one coherent fiber-optic equipped with an objective eyepieces at the other side.

In a fourth embodiment, two separate fiber-scopes are connected together, each with its own objective and eyepiece. Two independent images are presented to each eye, thus creating a stereo image of the area of interest.

DESCRIPTION OF THE DRAWINGS

For better understanding, the invention will now be described by way of example only. Reference will be made to the annexed drawings, which are not limiting. In the drawing:

FIGS. 3a and 3b are diagrammatic illustrations of the second embodiment of the invention; FIG. 3a is an elevational view, and FIG. 3b is a plan view;

DESCRIPTION OF PREFERRED EMBODIMENTS

Figure 1:
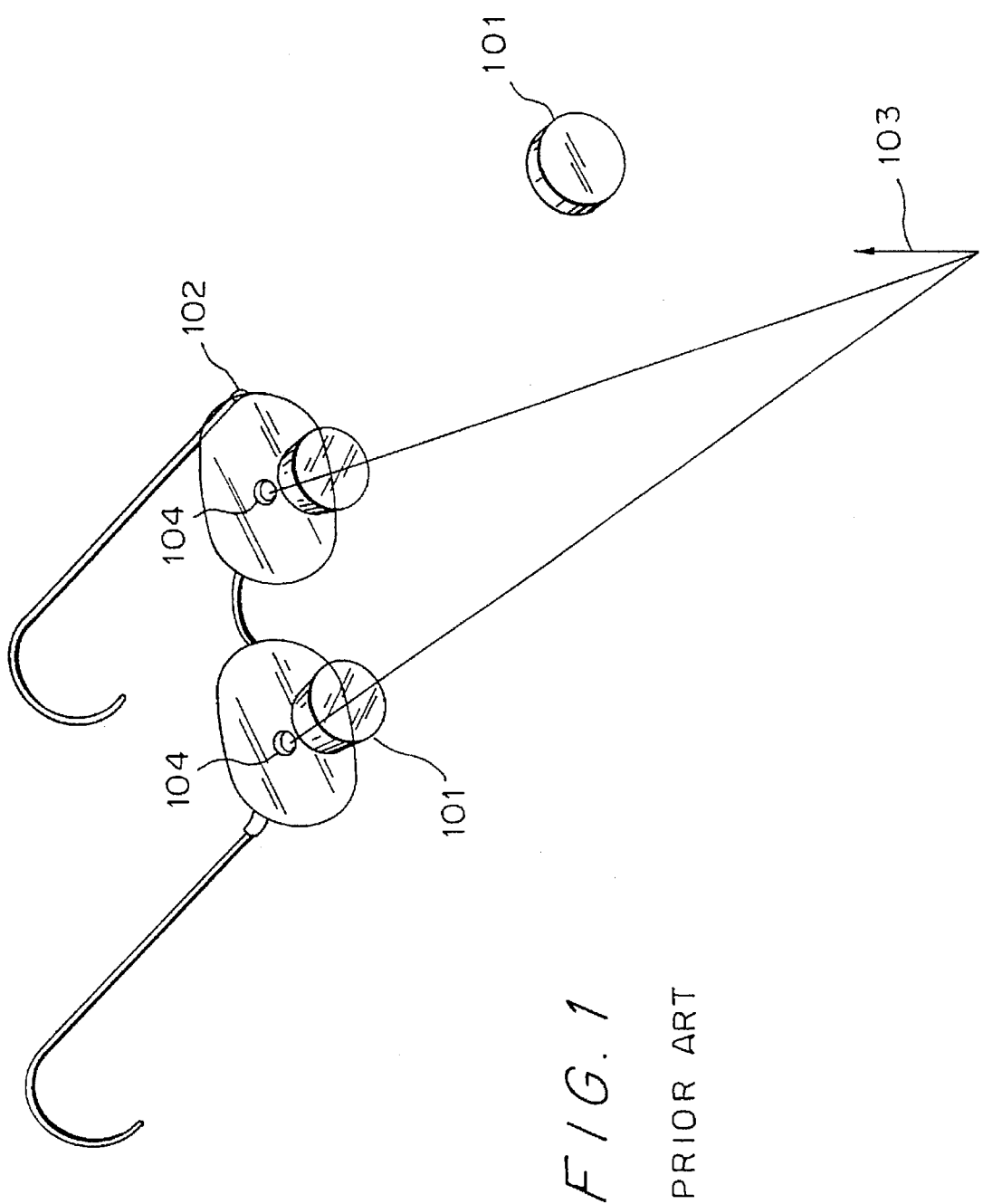
FIG. 1, labelled "prior art," is a diagrammatic illustration of prior-art spectacle based magnifiers.

FIG. 1 shows a prior-art spectacle system with a pair of magnifying lenses 101 installed in front of the spectacle's glass 102 by way of bonding or other mechanical attachment.

An object 103 placed in front of the spectacle can be observed by the user's eyes 104 through the regular spectacles 102 or through the magnification lens system 101 simply by a slight eye movement.

Figure 2:
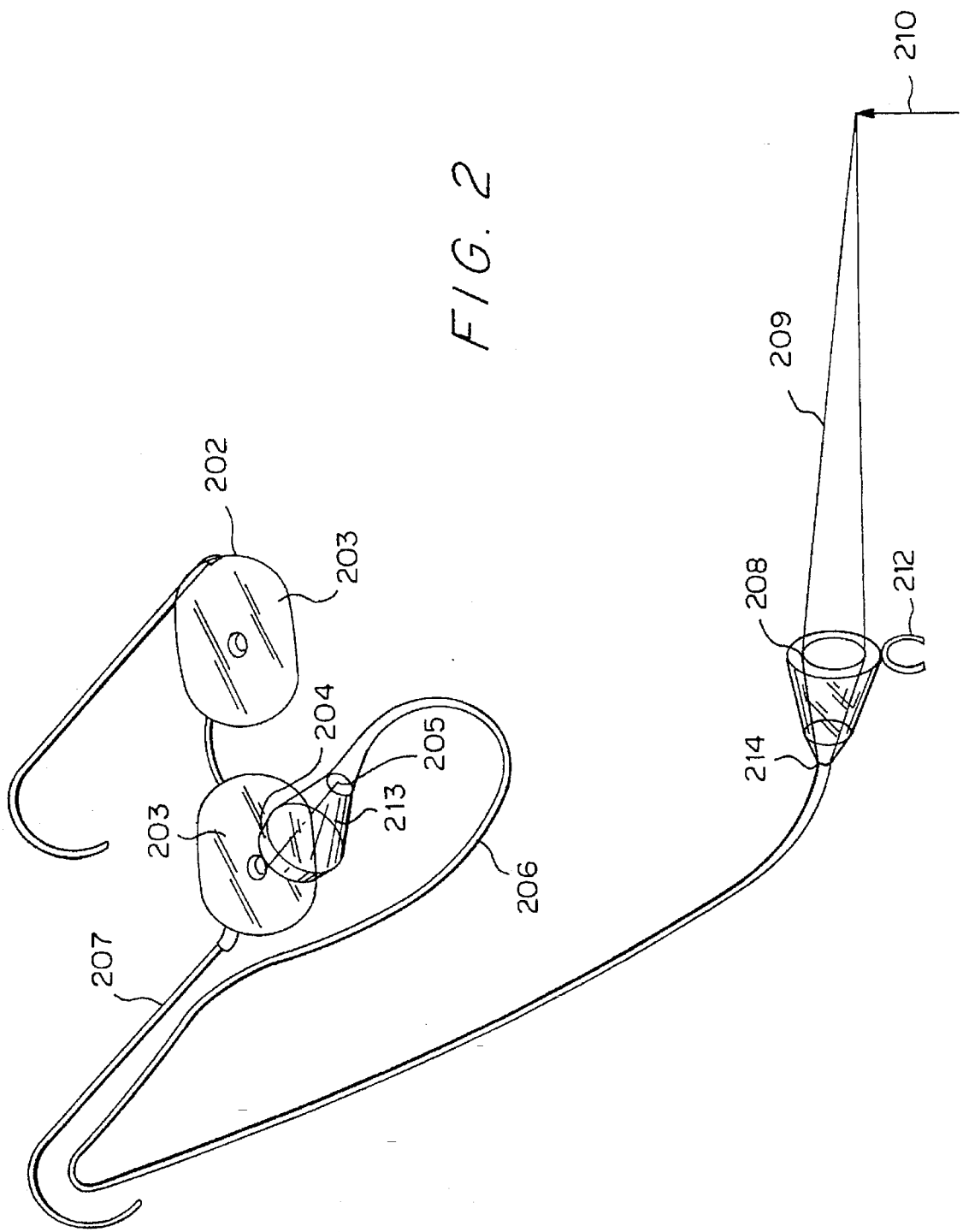
FIG. 2 is a diagrammatic illustration of a fiber-scope according to the first embodiment of the invention.

FIG. 2 illustrates the first embodiment of the present spectacle coherent optic magnifying system. This embodiment, as well as those detailed below, are described merely by the way of example. The principles disclosed are not limited by the specific embodiments.

A spectacle 202 equipped with glass optics 203 is displayed in FIG. 2. A fiber-scope is mounted on the spectacle. The eyepiece side of the fiber-scope is attached by mechanical means or bonding material (not shown) to the outer lower side of the spectacle glass 203 by blocking only a small part of the glass. The eyepiece 204 images and magnifies the end of the fiber, denoted as 205, and presents it to the user's eye. To allow for different users of this optical system, the eyepiece may be adjusted with respect to the fiber-optic bundle along the optical axis 213.

The coherent fiber bundle 206 is attached along the spectacle frame, denoted as 207. The end of the coherent fiber is connected to an objective lens 208.

Light rays 209 are collected from the observed object 210 by the objective lens 208 and imaged at one end of the coherent fiber bundle 214. The image is then transmitted through the coherent fiber bundle to the other end 205 and presented to the eye by means of eyepiece 204.

The objective side of the fiber optic device can be attached to a working tool (not shown in drawing) or to the user's hands by mechanical means, denoted by 212.

Figure 3B:
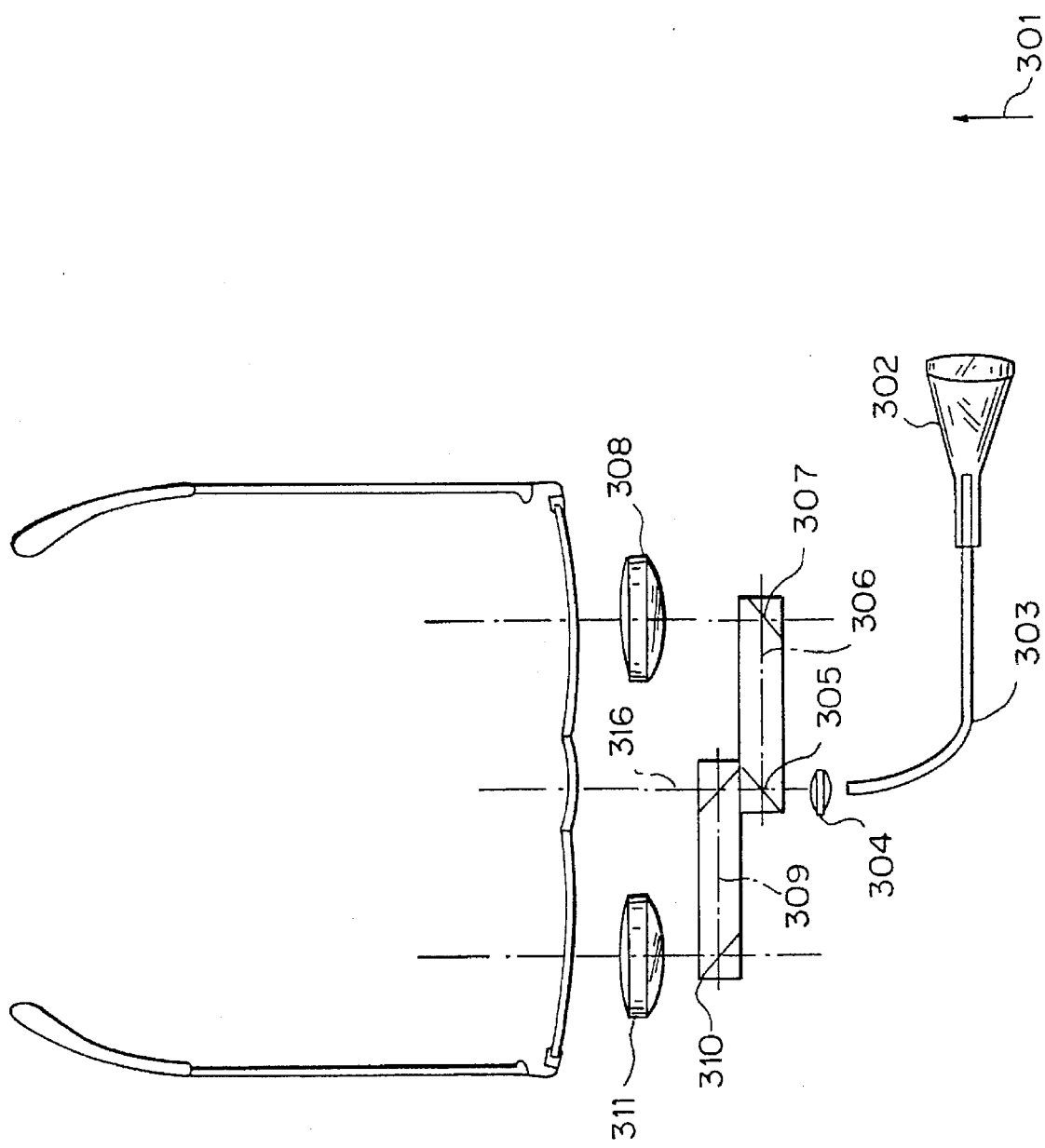

In the embodiment of FIG. 3a and FIG. 3b, the image emerging from the eyepiece end of the fiber-optic is split similarly to the one in FIG. 2 and simultaneously presented to both eyes by two eyepiece systems.

The image split is achieved by a combination of beam splitters and glass mirrors. One way of splitting the image and presenting it to the two eyes is demonstrated by way of example. Other beam splitting techniques could be implemented in this embodiment.

The image of the object 301 is collected by the objective lens 302 and imaged at the coherent fiber-optic bundle 303 in the same way as disclosed in FIG. 2. At the output end of the coherent fiber-optic bundle, the emerging image is collected by an additional lens 304 and is then split in two by a beam splitter 305. One part of the image is directed to the left eye along the path denoted as 306 and reflected towards the left eye by the mirror 307 parallel to the beam splitter. The image is then presented to the left eye by the left eyepiece 308.

The other part of the image is directed to the right eye along the axis 309, reflected by the right mirror 310 towards the right eye and presented by the right eyepiece 311. The two presented images create a 3-D image in the user's eye.

A special mechanical frame 313, shown in FIG. 3a, is used for mounting the beam splitter 305 with the left mirror 307 into a mechanical housing. A similar mechanical housing 314 is used for mounting the two parallel mirrors 310. The mechanical housings 313 and 314 are joined together by a rotary journal bearing (not shown) and are free to rotate around the axis 316, allowing the distance between the two eyepieces to be adjusted according the separation of the user's eyes.

Figure 4:
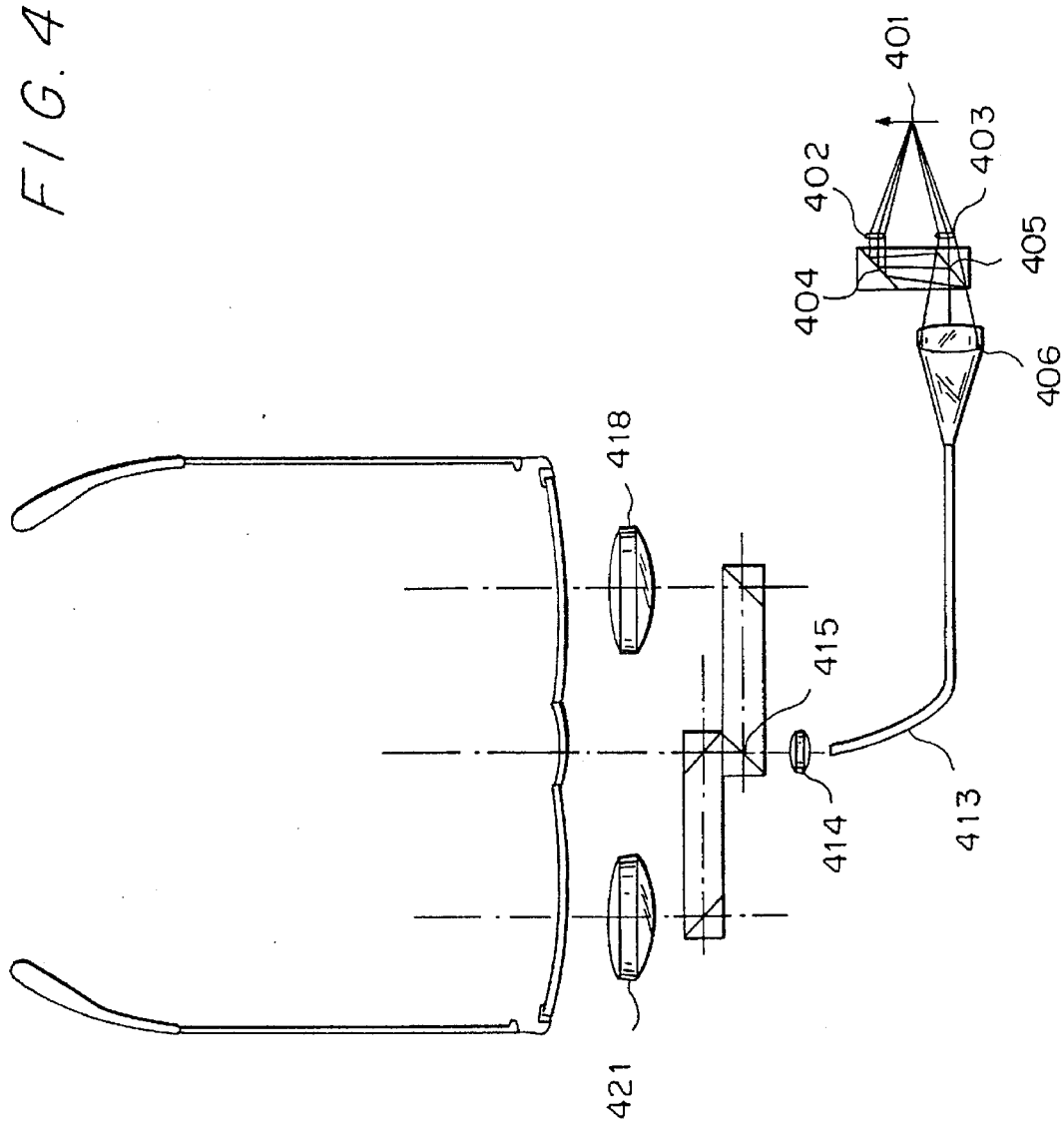
FIG. 4 is a diagrammatic illustration of the third embodiment of the invention.

Attention is now directed to FIG. 4, which illustrates in a schematic manner another embodiment where two images are collected by the same objective, each image being differently colored. The two images traveling through the coherent fiber-optic are then presented to the eyes by beam splitting similar to that shown in FIG. 3. The eyepiece side is identical to that in FIG. 3 with one exception: the beam splitter 305 in FIG. 3b is replaced with a similar beam splitter that splits the image into two differently colored images. This beam splitter is called a dichroic beam splitter.

The objective side of the system of FIG. 4 is significantly different from the one presented in FIG. 3. In FIG. 4 the object 401 is observed from two apertures 402 and 403 respectively. Note that aperture 402 is laterally offset from 403. The light rays which enter the aperture 402 are reflected by the mirror 404 towards a dichroic beam splitter 405. This beam splitter 405 reflects approximately half of the light spectrum towards the objective and transmits the other half. Light from aperture 403 will be transmitted through the same dichroic filter and only the colors which were not reflected from the aperture 402 will pass and reach the objective.

Two images, one from aperture 402 and the other from aperture 403, are now differently colored and are imaged by the same objective 406 at the coherent fiber bundle 413.

The images travel through the fiber 413 and are split at the eyepiece location by a similar means (414, 415) that was shown in FIG. 3. Then the images are displayed to the user's eyes through the eyepieces 421, 418. Each eye sees a different image, one from aperture 402 and the other from aperture 403, thus allowing stereo imaging through a single fiber optic bundle.

Figure 5:
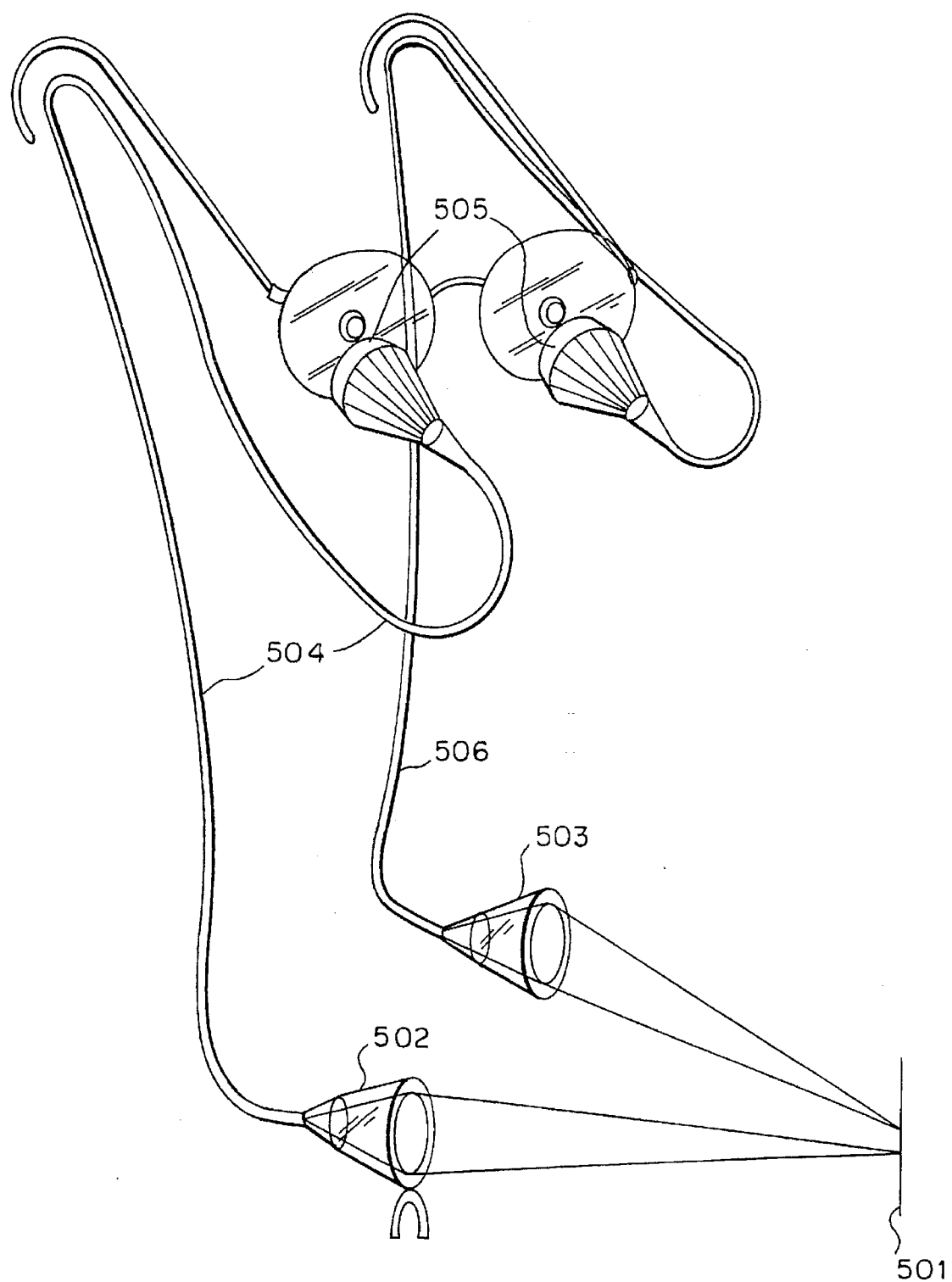
FIG. 5 is a diagrammatic illustration of the fourth embodiment of the invention.

In FIG. 5 another embodiment is disclosed, in which observation of 3-D scenery is performed through two coherent fiber optic bundles, where each of the bundles presents its image 502, 503 laterally offset from the other. Each objective images the object onto a different fiber-optic bundle 504, 506. The images from the bundles are then presented to the user's eyes by a pair of eyepieces 505, and a 3-D picture is created of remote scenery which is otherwise inaccessible. The eyepiece side could be attached to the user's spectacles 505, but the user can observe the scene by other means not necessarily attached to a pair of spectacles.

In the following claims:

"mechanical" includes adhesives or bonding as well as fasteners, etc; and

"spectacles" includes any head-mounted device allowing the invention to be supported near the user's eyes. It may include bare eyeglass frames without lenses, goggles, headbands, and the like.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. The means and materials for carrying out various disclosed functions may take a variety of alternative forms without departing from the invention. It is to be understood that the phraseology or terminology employed herein is for the purpose of description and not of limitation.

What is claimed is:

1. A fiber-scope system for use in conjunction with spectacles, comprising:

an objective lens for imaging the object;

an eyepiece;

a coherent fiber-optic bundle for optically coupling the eyepiece to the objective lens, the fiber-optic bundle having an objective end and an eyepiece end; and mechanical eyepiece means for attaching the eyepiece to the spectacles, in a position wherein a user wearing the spectacles view the object selectively through the spectacles and the system;

a left objective lens for imaging the object;

a right objective lens for imaging the object;

a left eyepiece;

a right eyepiece;

a coherent left fiber-optic bundle for optically coupling the eyepiece to the objective lens, the left fiber-optic bundle having a left objective end and a left eyepiece end; and a coherent right fiber-optic bundle for optically coupling the eyepiece to the objective lens, the right fiber-optic bundle having a right objective end and a right eyepiece end; and wherein the mechanical eyepiece means includes means for attaching the left eyepiece to the spectacles adjacent a left eye of the user and for attaching the right eyepiece to the spectacles adjacent a right eye of the user;

whereby the image is simultaneously viewed by a right eye of the user and a left eye of the user.

2. A fiber-scope system for use in conjunction with spectacles, comprising:

an objective lens for imaging the object;

an eyepiece;

a coherent fiber-optic bundle for optically coupling the eyepiece to the objective lens, the fiber-optic bundle having an objective end and an eyepiece end; and mechanical eyepiece means for attaching the eyepiece to the spectacles, in a position wherein a user wearing the spectacles view the object selectively through the spectacles and the system;

a left objective lens;

a right objective lens;

a left eyepiece;

a right eyepiece;

left mechanical eyepiece means for attaching the left eyepiece to the spectacles adjacent a left eye of the user;

right mechanical eyepiece means for attaching the right eyepiece to the spectacles adjacent a right eye of the user; and image splitting means, optically coupled to the eyepiece end of the fiber-optic bundle, the right eyepiece, and the left eyepiece, for splitting a combined image of the fiber-optic bundle into a right image at the right eyepiece and a left image at the left eyepiece; and whereby an image is simultaneously viewed by a right eye of the user and a left eye of the user.

3. The system according to claim 2, comprising first color-selective separation means in an image combining means and second color-selective separation means in the image splitting means, whereby selectively certain colors are associated with the right image and other colors are associated with the left image.

4. The system according to claim 3, wherein the first color-selective separation means and the second color-selective separation means each comprise a dichroic filter.

* * * * *